United States Patent [19]

Ruzicka et al.

[11] Patent Number: 4,597,298
[45] Date of Patent: Jul. 1, 1986

[54] HYDRODYNAMIC SAMPLE INTRODUCING SYSTEM

[75] Inventors: Jaromir Ruzicka, Holte; Elo H. Hansen, Lyngby, both of Denmark

[73] Assignee: Bifok AB, Sollentuna, Sweden

[21] Appl. No.: 683,941

[22] Filed: Dec. 18, 1984

Related U.S. Application Data

[63] Continuation of Ser. No. 385,049, Jun. 4, 1982, abandoned.

[51] Int. Cl.⁴ .............................................. G01N 1/02
[52] U.S. Cl. ................................................. 73/863.71
[58] Field of Search ........... 73/863.71, 864.81, 61.1 C; 422/81, 82

[56] References Cited

U.S. PATENT DOCUMENTS

| | | | |
|---|---|---|---|
| 3,475,128 | 10/1969 | Thiers | 436/52 |
| 3,488,154 | 1/1970 | Hronas | 422/81 |
| 3,511,080 | 5/1970 | Roof | 73/864.81 |
| 3,663,831 | 5/1972 | Cook | 417/12 X |
| 3,737,251 | 6/1973 | Berman et al. | 128/760 X |
| 3,827,304 | 8/1974 | D'Autry | 73/864.21 |
| 3,842,679 | 10/1974 | Iwao et al. | 73/864.81 X |
| 3,933,430 | 1/1976 | Hare | 422/81 X |
| 4,022,575 | 5/1977 | Hansen et al. | 436/52 |
| 4,155,978 | 5/1979 | Naono et al. | 422/81 X |
| 4,177,677 | 12/1979 | Ruzicka et al. | 73/864.81 |
| 4,224,033 | 9/1980 | Hansen et al. | 436/52 |
| 4,268,268 | 5/1981 | Blum | 436/52 |
| 4,314,824 | 2/1982 | Hansen et al. | 436/52 |

FOREIGN PATENT DOCUMENTS

1564788   4/1980   United Kingdom ................. 422/81

Primary Examiner—Stewart J. Levy
Assistant Examiner—Robert R. Raevis
Attorney, Agent, or Firm—Poms, Smith, Lande & Rose

[57] ABSTRACT

A sample introduction system comprises a sampling circuit and a carrier stream circuit where the two circuits share a volumetric conduit which is at all times connected to and simultaneously opened to both sampling and carrier circuits. This system allows, by a controlled combination of hydrostatic and hydrodynamic forces, to create a well-defined sample zone within the volumetric circuit and then to transport this zone, in a well-reproduced manner, into a continuous flow analyzer where an assay of sample solution components may be performed quantitatively, if necessary even with the aid of chemical reactions, from the signal as provided by a flow-through detector.

5 Claims, 7 Drawing Figures

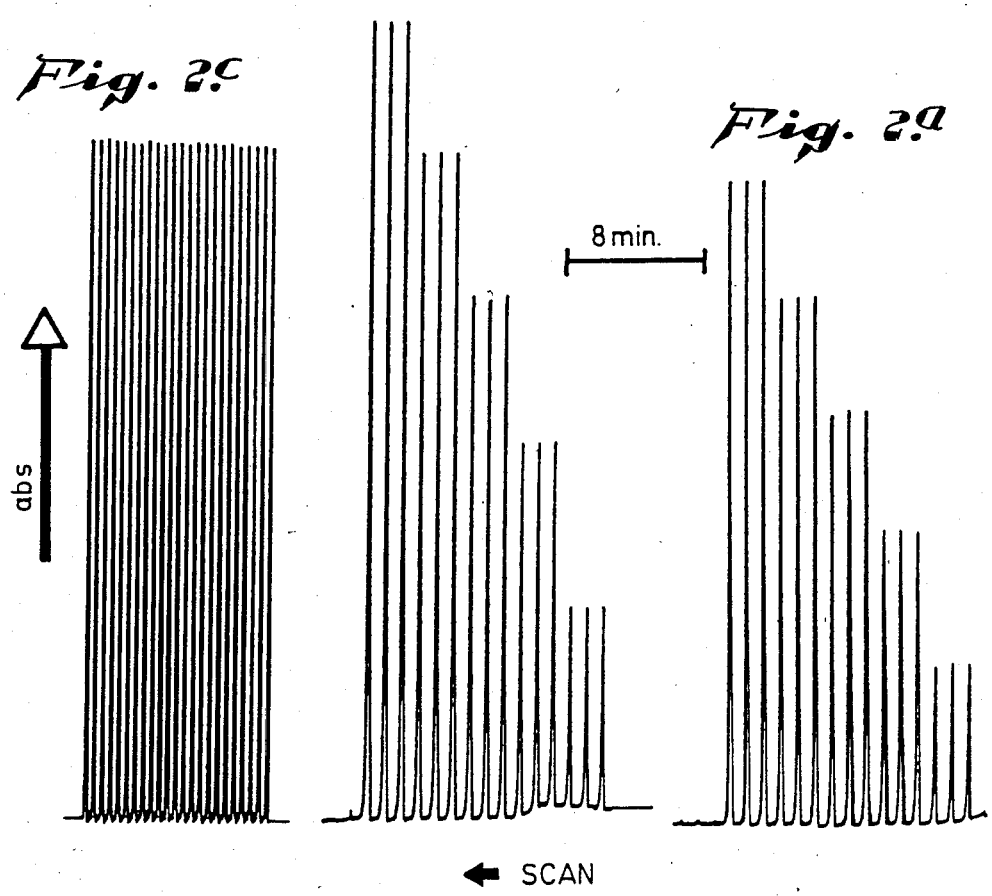

HYDRODYNAMIC SAMPLE INTRODUCING SYSTEM

This application is a continuation of Ser. No. 385,049 filed June 4, 1982, now abandoned.

BACKGROUND OF THE INVENTION

The present invention relates to a sample introduction methodology by means of which a volume of a liquid sample zone, which is to be introduced into an unsegmented liquid carrier stream, can be defined on the basis of a controlled combination of hydrostatic and hydrodynamic forces, said well-defined sample zone subsequently being transported to a flow-through analyzer in which a species present in the sample solution—possibly formed as a result of one or more chemical reactions taking place—can be evaluated quantitatively in a flow-through detector arrangement.

Assay by means of the Flow Injection Analysis (FIA) technique (see for example our U.S. Pat. Nos. 4,022,575 and 4,224,033) requires that a sample solution to be analyzed is introduced into an unsegmented carrier stream as a well-defined sample zone, the volume and geometry of which is strictly reproducible. The conventional sample introduction techniques can be divided into three groups which are based on the following principles:

(1) Direct injection of a precisely metered amount of sample solution into a carrier stream (see for example our U.S. Pat. No. 4,022,575);

(2) Insertion of a precisely metered amount of sample solution by means of a valve (see for example our U.S. Pat. No. 4,224,033); and (3) Intercalation of a precisely metered amount of sample solution by means of a system of magnetic valves (see for example our U.S. Pat. No. 4,177,677).

By the first-mentioned method of sample introduction, the sample solution is injected by means of a syringe provided with a hypodermic needle which is pierced through the wall of the conduit in which the carrier stream is propelled, but this method of introduction is however not always sufficiently reproducible, nor does it lend itself readily to automation. By the introduction method referred to in Group (2), the use of sliding or rotary valves with exact bores of precisely metered volume (or possibly also provided with external sample loops in order to accommodate larger sample volumes)—and where the sample bores partly can be brought in a position where they, with sample solution, are made to be part of the carrier solution circuit so that the samples can be brought to be transported by the carrier stream—is most common as it yields highly reproducible results and is easily automated. Its drawbacks are the high cost of the valves which must be very precisely machined, and the mechanical wear of the moving parts which must be kept leakproof even after thousands of injections. By the introduction method referred to in Group (3), use is made of several (at least four) magnetic valves which, in a certain sequence and at predetermined time intervals, can be opened and closed. Also this method of introduction lends itself readily to automation, but it requires obviously ancillary electronic timing circuitry. Its greatest drawback is however that the elastic components on which the magnetic open/close valves mechanically operate eventually become worn and deformed as a result of the repeated localized pressure exerted by the wedge of the magnetic valves, and thus with time might fail to open or close completely, which will result in a slowly increasing malfunction which can be extremely difficult to identify.

The common denominator of all three sample introduction designs mentioned above is that the metered volume of sample solution to be introduced is defined by the volume of a solid container (bore, loop length, etc.) which immediately prior to introduction of the metered sample zone into the carrier stream is hermetically closed (that is, by introduction method 1 the metered volume of liquid sample corresponds to the volume trapped under the plunger of the hypodermic syringe; by introduction method 2 the liquid in the closed container is represented by that volume of sample liquid which is enclosed within the bore or sample loop of a sliding or rotary valve while the valve is being switched from the sampling to the introduction position; and by introduction method 3 the closed container, and the metered volume therein, corresponds to that volume which the magnetic valves entrap in a tube or conduit of a given length and diameter).

A problem which all three of these sample introduction systems have is that the closed container or conduit in which the well defined sample volume is placed or entrapped must continually be switched into and out of the carrier stream circuit or conduit during sample injection and sample loading. When the sample solution is being loaded into the closed sample container or conduit, the sample container must be disconnected or otherwise separated from the carrier flow stream. When the sample is to be introduced or injected into the carrier stream, the sample container must be switched into the system or otherwise connected so that the carrier stream sweeps through the container to transfer the sample solution into the carrier solution circuit or otherwise allows for the sample solution to be transferred from the sample container to the carrier stream circuit. This type of sample introduction or injection technique requires the use of numerous mechanical devices such as the valves and syringes discussed above which each have their own inherent drawbacks.

SUMMARY OF THE INVENTION

In accordance with the present invention a sample introduction system and method are provided in which the metered volume of sample solution which is introduced into the carrier stream system or circuit is not defined or measured by the volume of a closed container or circuit as required by the previously discussed sample introduction designs.

The present invention is based upon a sample introduction technique in which the sample container or conduit is permanently connected to the carrier stream circuit at all times and in fact forms a common part of the carrier stream circuit. The sample solution and reagent stream are passed through this common carrier stream and sample conduit by using hydrodynamic and hydrostatic forces only without the need for mechanical control devices such as valves.

The sample introduction system in accordance with the present invention includes a carrier stream conduit through which an unsegmented liquid carrier stream is flowed. The carrier stream conduit includes an inlet, an outlet and a volumetric conduit portion having an upstream end and a downstream end and which defines a sample zone having a sample volume. A sample stream conduit is provided through which the sample solution is flowed. The sample stream conduit includes an inlet, an outlet and a volumetric conduit portion which is common to the carrier stream conduit. Both the carrier stream conduit and sample stream conduit have a common inlet into the upstream end of the volumetric conduit. They both also have a common outlet from the downstream end of the volumetric conduit. Carrier stream pump means and sample solution pump means such as peristaltic pumps are provided to controllably and selectively pump both the carrier stream and sample solution through the carrier stream volumetric conduit portion. The pumping of the carrier stream and sample solution are controlled so that the carrier stream flow into the volumetric conduit is stopped while the sample solution is pumped into the upstream end and through the volumetric conduit portion. After the volumetric conduit portion is filled with sample solution, the sample solution flow is stopped and the carrier stream is again pumped or flowed through the volumetric conduit portion to thereby sweep the well-defined sample volume present in the volumetric conduit portion into the carrier stream circuit. Subsequent samples of sample solution are introduced into the carrier stream by repeating the above steps where the carrier stream flow into the volumetric conduit is stopped, the sample flow through the volumetric conduit started, the sample flow stopped after the conduit is filled with sample solution and the carrier stream started again.

The above described system and method in accordance with the present invention allows sample solution introduction into the carrier stream without using valves. The hydrostatic and hydrodynamic forces of the alternately stopped and flowing carrier stream and sample stream at the inlets to the upstream end of the volumetric conduit and at the outlets to the downstream end of the volumetric conduit make it possible to introduce a well defined volume of sample solution into the carrier stream using a conduit portion which is at all times common to both the sample solution conduit and carrier stream conduit. Therefore, in our invention that container which serves for metering the volume of the sample zone can thus be permanently connected to and at all times opened to both the sampling and the carrier stream circuits; that is, be one for both circuits' common portion of conduit. The obvious advantage of such a sample introduction system is the simplicity of construction and the total absence of any moving parts, which not only makes the hydrodynamic sample introduction system extremely reliable but also, in fact, completely maintenance-free and thus long-lasting.

The invention will be described in more detail in the following, and in this connection reference will be made to the accompanying figures.

BRIEF DESCRIPTION OF THE DRAWINGS

FIGS. 2A–C are recorder graphs or printouts showing the results of examples set forth in the specification.

DETAILED DESCRIPTION OF THE INVENTION

Figure 1A:
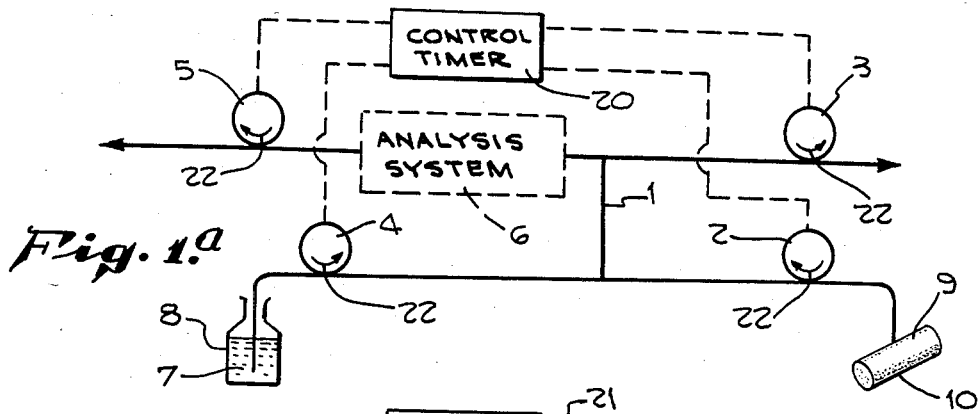
FIG. 1A is a diagram of a preferred sample introduction system in accordance with the present invention.

FIG. 1A states the components of the system which are:

(a) a sample introduction container or volumetric conduit 1 consisting of a given length of conduit (e.g. tube) of small inner diameter (typically 0.5 mm i.d., and typically of a length of 5 to 100 cm, depending on the volume of sample solution which is to be introduced);

(b) liquid propelling means 2, 3, 4 and 5 (e.g. peristaltic pumps), partly to serve the sampling circuit by simultaneous operation of 2 and 3, and partly to serve the carrier stream circuit by simultaneous operation of 4 and 5; and (c) a timing device, such as the control timer shown schematically at 20 is provided to control the liquid propelling aggregates 2, 3 and 4, 5, respectively, so that these can either be stopped (STOP) or activated (GO). It is essential that the liquids are delivered in the directions shown by the arrows 22, and that the liquid propelling devices used effectuate that the columns of liquid present in each indiviual circuit, except the one present in that portion of the conduit which is common for both circuits, is kept completely still when the liquid propelling devices (pumps) belonging to each individual circuit are not activated. Furthermore, it is necessary that the volumetric pumping rates in and out of the sampling circuit is as close to unity as possible, which requires that pumping aggregates 2 and 3 operate at exactly the same volumetric pumping rates. This is however very easily accomplished, for instance by using a two-channel peristaltic pump equipped with two identical pumping tubes. Exactly the same requirements to identify for in and out pumping of liquid apply for the carrier stream circuit, served by pumping devices 4 and 5. During the sampling cycle, sample solution 9 is drawn from a source 10 to be monitored (this might for instance be a reactor in which a chemical reaction takes place which has to be controlled, or it can be a pipe transporting a given solution, or it may possibly be a blood artery) by means of pumping devices 2 and 3 until the volumetric conduit 1 is thoroughly flushed and filled all along its length with sample solution. During the entire sampling cycle, pumping devices 4 and 5 are kept deactivated and therefore the columns of liquid 24 and 26 to the left of conduit 1 will prevent any sample solution to enter the carrier stream circuit. After the sampling cycle has been completed, pumps 2 and 3 are stopped while pumps 4 and 5 are activated, thus introducing a well-defined sample zone (i.e., corresponding to the length of conduit 1) into the flow-through analysis system 6, in which possible chemical reaction and subsequent detection of the introduced sample takes place. Detection is provided by a flow through detector or other well known detector which is part of the analysis system 6. Because pumps 2 and 3 are now kept deactivated; that is, the columns of liquid to the right of conduit 1 are now stationary, only that amount of sample solution which was originally present in conduit 1 can be transported into the analyser system 6, namely by means of carrier solution 7 aspirated from reservoir 8. The carrier solution is thus, during this second cycle, the only moving liquid stream through the system, and pumps 4 and 5 are kept activated until the entire dispersed sample zone has passed the analyser system 6 which is indicated, on a recorder connected to the detector, by the registered signal returning to the baseline and thus reporting that the carrier solution cycle has been completed. Pumps 4 and 5 can then be stopped while pumps 2 and 3 may be restarted to begin a new measuring cycle. As the sampling and carrier cycles totally may be completed within one minute or less, the system is well-suited for e.g. continuous monitoring of industrial processes or medical applications such as critical patient care supervision.

By the application described above, the sample solution is introduced into the analysis system intermittently. It is however also possible to use the depicted system for continuous measurement of a given sample stream, while the hydrodynamic sample introduction principle is now used to verify the calibration of the applied flow-through analyser simply by introducing intermittently a standard solution of that species which is continuously being monitored; that is, it can be said that the roles of the sample and carrier streams here have been reversed. This may be illustrated by referring to FIG. 1A where pumps 2 and 5, simultaneously and with identical volumetric pumping rates, now continuously aspirate that solution 9 which is to be monitored, and which solution is propelled via conduit 1 to the analyser 6. During this procedure, pumps 4 and 3 are deactivated, and the columns of liquid belonging to this circuit—except the volume present in that portion of conduit which is common for both circuits, i.e. 1—is kept still. When the analyser is to be adjusted or recalibrated, pumps 2 and 5 are stopped and pumps 4 and 3, which both pump with identical volumetric pumping rates, are activated. By this procedure the volumetric conduit 1 is filled with standard solution 7 from reservoir 8, and when pumps 4 and 3 are stopped and pumps 2 and 5 reactivated, the standard solution zone metered in conduit 1 will be transported by the sample solution 9 into the analyser 6 and here give rise to a signal which, in respect to the continuously registered sample signal, can be used for adjusting or recalibrating the flow-through analyser.

Figure 1B:
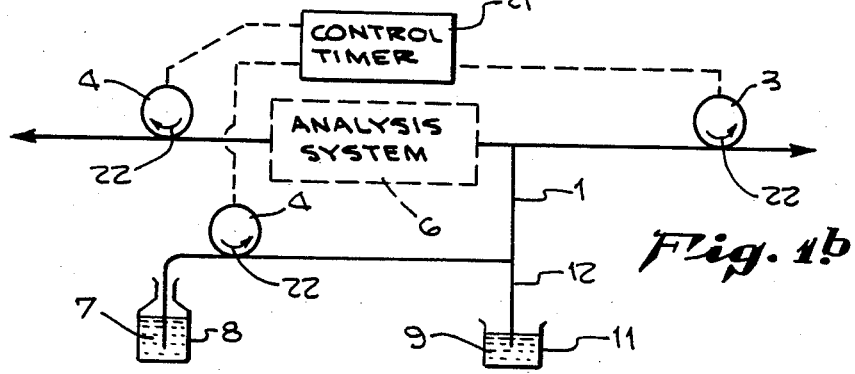
FIG. 1B is a diagram of an alternate preferred embodiment in accordance with the present invention.

If the volume of sample material available is limited and/or the sample cycle has to be kept short, as is often the case when analyzing larger series of discrete samples, the hydrodynamic sample introduction system can be modified and further simplified, as depicted in FIG. 1B. Here, sample solution 9 is aspirated from a sample cup 11, placed for example on a sample or a sample tray, via a conduit 12 which is made as short as practically possible, and runs from here into conduit 1, as drawn by activation of pumping device 3, the sampling cycle being limited to last as long as the volumetric conduit 1 is entirely flushed and filled with sample solution 9. As in the first-described example, pumps 4 and 5 are kept deactivated during the sampling cycle and are restarted only when the content of conduit 1 is to be introduced into the flow-through analyser 6 at which point of time pump 3 is stopped. A timing device, such as the control timer shown schematically at 21 is provided to control operation of the pumps 3, 4 and 5 as represented by the phantom lines connecting the control timer 21 and pumps 3, 4 and 5. It should be emphasized that in the absence of the controlling pump (sic 2 in FIG. 1A), the volumetric pumping rates of pumps 4 and 5 must be exactly identical because (a) if pump 4 pumps faster than pump 5, then the difference in the volumetric delivery rates of the carrier stream 7 will cause that part of the carrier stream from reservoir 8 will be forced to cup 11 and thus diluting the sample material before the next sampling cycle; or (b) if pump 4 pumps slower than pump 5, then some of the sample material 11 will be aspirated even during the carrier cycle and thereby cause a false signal on the recorder, registered as an increase of the baseline signal. However, the fact that a satisfactory balance can be achieved, and reproducibility can be maintained, is demonstrated in FIGS. 2A, B and C, which figures are photographic reproductions of the recorder signals obtained in a series of spectrophotometric measurements as registered by the analysis system 6 equipped with a flow-through cell placed in a spectrophotometer which was connected to a chart recorder so that it was possible continuously to monitor the absorbance (abs) of the carrier stream, which in itself was colourless. Thus, by injecting a dye solution as sample solution 9 into the system—and in the present case aqueous solutions of bromothymol blue (BTB) were used, the colour of which can be registered photometrically at 620 nm—the sample will during its passage of the analyser system 6 be registered as a peak, the height of which will be proportional to the intensity of colour present which again will be proportional on the one hand to the concentration of colour of the sample introduced into conduit 1 and on the other hand to the volume of sample metered in conduit 1; that is, at fixed sample volume (fixed volume of conduit 1) the peak height will be directly proportional to the concentration of colour in the sample solution 9. In FIG. 2A there is first shown a series of 15 sample introductions where a sample volume of 25 $\mu$l was used (that is, conduit 1 consisted of 12.5 cm tubing of an internal diameter of 0.5 mm), and where five different sample solutions of BTB of gradually increasing concentration were each introduced in triplicate; these solutions were prepared from an aqueous stock solution of BTB by successive dilution with water, the volumetric ratio of stock solution and water in the five solutions being 1:4, 2:3, 3:2, 4:1 and 5:0 respectively.

Then the same experiment was repeated but this time 50 $\mu$l aliquots of dye solutions were introduced (FIG. 2B); that is, conduit 1 consisted of 25 cm of 0.5 mm i.d. tubing. As seen from FIGS. 2A and B, these two series of experiments demonstrate the excellent reproducibility which can be obtained by the hydrodynamic sample introduction method. The last series of sample introductions, shown in FIG. 2C, comprises 23 sample introductions obtained over a period of 23 minutes (the attached recorder being run at a lower chart speed than in experiments 2A and B) and where each time 50 $\mu$l of the same 4:1 BTB sample solution was introduced. Not only does this experiment show excellent reproducibility of measurement, but the system exhibits furthermore a very high degree of stability in time.

Figure 1C:
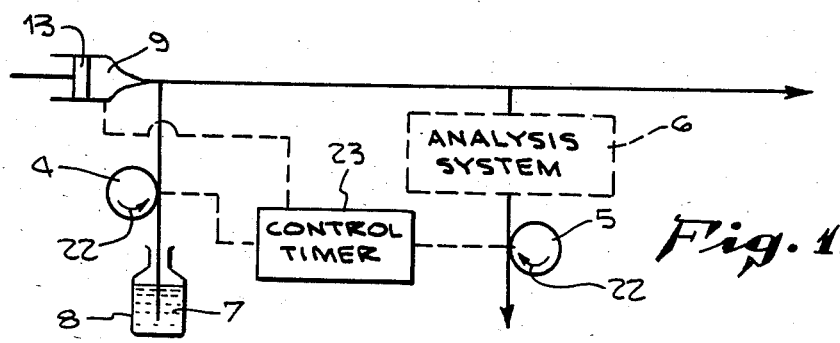
FIG. 1C is a diagram of another alternate preferred embodiment in accordance with the present invention.

With reference to FIG. 1C, yet another embodiment of the hydrodynamic sample introduction system will be discussed. The sample solution pumping aggregate is replaced by a piston device such as a syringe 13, containing sample solution 9, which serves for introduction of sample solution via the sample circuit into the volumetric conduit 1, the length and cross-sectional area of which define the sample zone volume. Thus, only two means 4, 5 of solution propelling are needed such as, for example, a two-channel peristaltic pump which, after the sample circuit and conduit 1 have been filled with the sample solution, are started, thus introducing the sample zone into the carrier stream conduit and further into the analyser 6. A timing device, such as the control timer shown schematically at 23 is provided to control operation of syringe 13 and pumps 4 and 5 as represented by the phantom lines connecting the control timer 23 and syringe 13 and pumps 4 and 5. A necessary prerequisite for satisfactory performance of this embodiment is that the piston in device 13 is held in a fixed position during the operational period of the carrier stream cycle, and that the pumping rates within channels 4 and 5 are identical. The advantage of this approach is the simplicity of the experimental setup; and the possibility of manipulating small sample volumes anaerobically from a donor source such as a patient, for example, into the analytical system. A possible drawback, if the syringe would be operated manually, is the necessity of skilled handling.

Figure 1D:
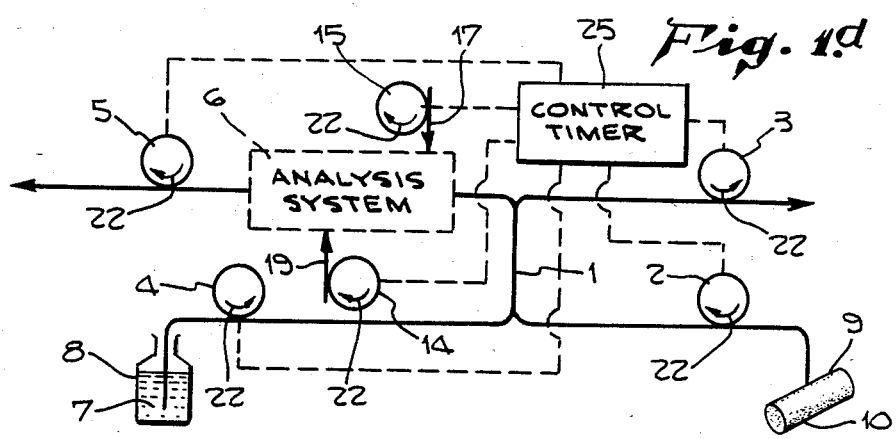
FIG. 1D is a diagram of an additional preferred embodiment in accordance with the present invention.

It should be emphasized that modifications of the invention described above do not affect its basic concept. Such modifications may comprise (a) Replacing one of the solution propelling aggregates, functioning in pairs and servicing the sample solution circuit (such as the pair 2,3 in FIG. 1A) and/or the carrier stream circuit (such as the pair 4,5 in FIG. 1A), by an open-closed valve which is in open position while the corresponding solution propelling means is active, and in closed position while the corresponding solution propelling means is inactive;

(b) As shown in FIG. 1D, pumps 14 and 15 may be added to the system of FIG. 1A to provide a system through which additional streams 17 and 19 which may contain liquid reagents for reaction with the sample can be added, or withdrawn, from the analysis system 6, provided that the delivery rates are balanced so that exactly the same amount of liquid is delivered into the volumetric conduit 1 by means of propelling means 4 as is leaving it at the opposite end, which requires that the aspirational rate of means 5 must be equal to the net sum of delivery rates of means 4, 14 and 15. Alternatively, pumping aggregate 5 may be replaced by an open-closed valve, with the modifications described in paragraph (a). A timing device, such as the control timer shown schematically at 25 is provided to control operation of pumps 2, 3, 4, 5, 14 and 15 as represented by the phantom lines connecting the control time 25 and the pumps;

(c) Addition of one or several volumetric conduits 1, 1', 1" etc., as these can be placed in series in the sampling circuit so that each individual volumetric conduit is serviced by a separate carrier stream with the aim of performing analyses in a number of analysers 6, 6', 6" etc., arranged in parallel, as all what is needed is hydrodynamic and hydrostatic balance and suitable sequential timing of the operating cycles of the sample and carrier stream circuits;

(d) Another possible modification is that in the embodiment shown in FIG. 1 one may continue to pump the sample solution 9 by means of the synchronized sample solution propelling means 2, 3 even after the carrier stream circuit propelling means 4, 5 have been activated so that also the carrier stream 7 is in motion. Thus the volume of sample solution will be increased over that volume which may be accommodated within conduit 1 while solutions are still. The increase of the introduced sample volume depends on the length of the time period during which the operational cycle of the sampling circuit and the operational cycle of the carrier stream circuit overlap each other, and the respective pumping rates generated by the solution propelling means 2, 3, 4 and 5. The advantage of this approach is that it opens possibilities flexibly to vary the volume of the introduced sample solution by means of electronic control of the repetitive STOP/GO intervals comprising the operational cycles of the respective circuits. The drawback of this particular sample introduction embodiment in accordance with the present invention is that the reproducibility of the introduced sample volumes depends on an exact timing of the operational cycles and on the pumping and aspiration rates of the liquid propelling means 2, 3, 4 and 5. The previously described embodiments in which the flow of the carrier stream and sample stream into the volumetric conduit is alternately stopped and started is independent on these parameters.

Though typical applications and embodiments of the present invention were illustrated by several examples, it should be understood that further variations and modifications of the constructions, materials and components described above are possible without deviation from the spirit of the invention, the scope of which is defined in the following claims.

What we claim is:

1. A method for introducing a volume of liquid sample into a liquid carrier stream in a continuous liquid flow analysis system comprising the steps of:

flowing a liquid carrier stream through a conduit having a common inlet through which said carrier stream and a liquid sample stream are both introduced into said conduit, a volumetric conduit portion defining a sample zone having a sample volume and a common outlet through which said carrier stream an said sample stream are both removed from said conduit wherein flowing said carrier stream through said conduit is provided by pumping said carrier stream into said conduit at a location upstream from said conduit and simultaneously pumping said carrier stream from said conduit at a location downstream from said conduit;

maintaining said sample stream in flow communication with both said common inlet and outlet during flow of said carrier stream therethrough, and wherein the flow of said sample stream is stopped during flow of said carrier stream through said conduit;

stopping the flow of said carrier stream through said common inlet into said conduit wherein stopping of said carrier stream flow is provided by simultaneously stopping said pumping at said upstream and downstream locations;

maintaining said carrier stream in flow communication with said volumetric conduit portion at said common inlet and outlet during flow of said sample stream therethrough;

flowing said sample stream through said common inlet, volumetric conduit portion and common outlet to provide a liquid sample volume equal to said sample volume in said volumetric conduit portion;

stopping the flow of said sample stream through said volumetric conduit portion; and flowing the carrier stream through said conduit to sweep said sample volume from said volumetric conduit portion to thereby introduce said sample volume into said carrier stream.

2. A method according to claim 1 wherein said method is carrier out in repeated sequences to introduce a series of liquid sample volumes into said carrier stream.

3. A method according to claim 1 wherein the liquid sample volume after introduction into said liquid carrier stream is passed with said carrier stream to an analysis system for measurement of a sample characteristic.

4. A method according to claim 3 including the additional step of adding one or more additional streams to said liquid carrier stream after introduction of said liquid sample volume into said carrier stream.

5. A method for introducing a volume of liquid sample into a liquid carrier steam in a continuous liquid flow analysis system comprising the steps of:

flowing a liquid carrier stream through a conduit having a common inlet through which said carrier stream and a liquid sample stream are both introduced into said conduit, a volumetric conduit portion defining a sample zone having a sample volume and a common outlet through which said carrier stream and said sample stream are both removed from said conduit;

maintaining said sample stream in flow communication with both said common inlet and outlet during flow of said carrier stream therethrough, and wherein the flow of said sample stream is stopped during flow of said carrier stream through said conduit;

stopping the flow of said carrier stream through said common inlet into said conduit;

maintaining said carrier stream in flow communication with said volumetric conduit portion at said common inlet and outlet during flow of said sample stream therethrough;

flowing said sample stream through said common inlet, volumetric conduit portion and common outlet to provide a liquid sample volume equal to said sample volume in said volumetric conduit portion wherein flowing said sample stream through said conduit is provided by pumping said sample stream into said conduit at a location upstream from said conduit and simultaneously pumping said sample stream from said conduit at a location downstream from said conduit;

stopping the flow of said sample stream through said volumetric conduit portion and wherein stopping of said sample stream is provided by simultaneously stopping said pumping at said upstream and downstream locations; and flowing the carrier stream through said conduit to sweep said sample volume from said volumetric conduit portion to thereby introduce said sample volume into said carrier stream.

* * * * *